United States Patent
Green

(10) Patent No.: US 8,404,270 B2
(45) Date of Patent: Mar. 26, 2013

(54) METHOD OF REDUCING INCIDENCE OF INTRAOCULAR PRESSURE ASSOCIATED WITH INTRAOCULAR USE OF CORTICOSTEROIDS

(75) Inventor: Ken Green, Marietta, GA (US)

(73) Assignee: Alimera Sciences, Inc., Alpharetta, GA (US)

( * ) Notice: Subject to any disclaimer, the term of this patent is extended or adjusted under 35 U.S.C. 154(b) by 199 days.

(21) Appl. No.: 12/974,738

(22) Filed: Dec. 21, 2010

(65) Prior Publication Data

US 2011/0150967 A1   Jun. 23, 2011

Related U.S. Application Data

(60) Provisional application No. 61/289,761, filed on Dec. 23, 2009.

(51) Int. Cl.
*A61F 2/14* (2006.01)

(52) U.S. Cl. .......... 424/427; 424/400; 424/422

(58) Field of Classification Search .............. None
See application file for complete search history.

(56) References Cited

U.S. PATENT DOCUMENTS

| | | | |
|---|---|---|---|
| 2004/0121014 A1* | 6/2004 | Guo et al. | 424/471 |
| 2007/0059336 A1 | 3/2007 | Hughes et al. | |
| 2009/0104243 A1 | 4/2009 | Utkhede et al. | |

OTHER PUBLICATIONS

International Preliminary Report on Patentability, PCT/US2010/061562, Jun. 26, 2012.
International Search Report, PCT/US2010/061562, Mar. 7, 2011, 2pp.

\* cited by examiner

*Primary Examiner* — Nissa Westerberg
(74) *Attorney, Agent, or Firm* — Brinks, Hofer, Gilson & Lione

(57) ABSTRACT

A method of treating an ocular disease in a subject using a corticosteroid with reduced incidence of intraocular pressure lowering surgery comprises injecting an intravitreal insert capable of providing a therapeutic effect for an extended period of time. The intravitreal insert delivers sustained sub-microgram levels of corticosteroid.

20 Claims, 4 Drawing Sheets

METHOD OF REDUCING INCIDENCE OF INTRAOCULAR PRESSURE ASSOCIATED WITH INTRAOCULAR USE OF CORTICOSTEROIDS

RELATED APPLICATIONS

The present patent document claims the benefit of the filing date under 35 U.S.C. §119(e) of Provisional U.S. Patent Application Ser. No. 61/289,761, filed Dec. 23, 2009, which is hereby incorporated by reference.

BACKGROUND

Diabetes mellitus, and its systemic and ophthalmic complications, represent an enormous public health threat in the United States. According to the CDC, the number of Americans diagnosed with diabetes has increased from approximately 8.1 million people in 1994 to approximately 17.9 million people in 2007. All patients with diabetes are at risk of developing some form of diabetic retinopathy, an ophthalmic complication of diabetes that presents with symptoms including the swelling and leakage of blood vessels within the retina or the abnormal growth of new blood vessels on the surface of the retina. According to the American Diabetes Association, in the United States diabetic retinopathy causes approximately 12,000 to 24,000 new cases of blindness each year making diabetes the leading cause of new cases of blindness in adults aged 20 to 74. Diabetic Macular Edema (DME), the primary cause of vision loss associated with diabetic retinopathy, is a disease affecting the macula, the part of the retina responsible for central vision. When the blood vessel leakage of diabetic retinopathy causes swelling in the macula, the condition is called DME. The onset of DME is painless and may go undetected by the patient until it manifests with the blurring of central vision or acute vision loss. The severity of this blurring may range from mild to profound loss of vision. The Wisconsin Epidemiologic Study of Diabetic Retinopathy found that over a ten-year period approximately 19% of diabetics studied were diagnosed with DME. As the population of diabetics increases, it is expected that the annual incidence of diagnosed DME will increase.

The current standard of care for the treatment of DME is laser photocoagulation. Laser photocoagulation is a retinal procedure in which a laser is used to cauterize leaky blood vessels or to apply a pattern of burns to reduce edema. This procedure has undesirable side effects including partial loss of peripheral and night vision. As a result of these side effects and a desire for improved visual outcomes, retinal specialists have supplemented laser photocoagulation with alternate off-label therapies for the treatment of DME, including injections of corticosteroids and anti-VEGF agents. Corticosteroids have been shown to improve visual acuity in DME patients in non-pivotal clinical trials, but are associated with increased intraocular pressure (IOP), which may increase the risk of glaucoma and cataract formation. Both of these alternate therapies are currently limited by a need for multiple injections to maintain a therapeutic effect.

Intravitreal Triamcinolone Acetonide Injections (IVTA) have also been used to treat DME. Triamcinolone acetonide is a corticosteroid administered via an intravitreal injection either as an adjunct to laser photocoagulation or as a stand-alone treatment. Typically administered in a 4,000 microgram (μg) suspension, IVTA is relatively inexpensive and has demonstrated temporary visual improvement and reduction of edema in patients with DME. Due to the potential side effects, including increased IOP, which may increase the risk of glaucoma and cataract formation, as well as the need for multiple injections, the use of IVTA for the treatment of DME is not optimal.

Additionally, a 0.7 mg free-floating, three to five month dexamethasone intravitreal implant is available for the treatment of DME following branch or retinal vein occlusion.

Anti-VEGF Intravitreal Injections have also been used to treat DME. Anti-VEGF therapies are administered via an intravitreal injection. VEGF has been identified as an important mediator in diabetic retinopathy, including DME, and appears to play a role in increasing vascular permeability in this condition. Similar to IVTA, anti-VEGFs require multiple injections, potentially as frequently as once per month, to sustain a therapeutic effect. Studies suggest that, in DME, corticosteroids appear to be therapeutically superior to anti-VEGF therapy.

Additionally, intraocular implants have been used in the treatment of ocular diseases other than DME. An exemplary implant marketed by Bausch & Lomb under the name RETISERT® is a sustained release, intravitreal implant with fluocinolone acetonide (FA) as the active corticosteroid. RETISERT® has been used to treat uveitis. This implant is affixed to the eye at the pars plana and is designed to provide controlled release of FA for approximately two and half years. The implant is available in 0.59 mg and 2.1 mg dosage forms.

A need exists for an effective treatment for ophthalmic complications related to diabetes mellitus that requires fewer injections and reduces the incidence of adverse side effects.

BRIEF SUMMARY

In accordance with a first aspect of the invention, a method of treating an ocular disease in a subject using a corticosteroid, wherein the incidence of IOP lowering surgery at 1 year or more after treatment is less than 10% comprises injecting at least one free-floating intravitreal insert comprising a dosage of corticosteroid into an eye of the subject such that the intravitreal insert settles near the base of the eye. The at least one intravitreal insert is configured to release the corticosteroid in a controlled manner over a time period of at least one year.

In a feature of this aspect, the ocular disease is diabetic macular edema. In another feature, the incidence of TOP lowering surgery at 1 year after treatment is less than 5%. In other features, the incidence of IOP lowering surgery at 2 years after treatment is less than 10% and/or is less than 5%. In yet other features, the incidence of IOP lowering surgery at 3 years after treatment is less than 30% and/or is less than 20% and/or is less than 10%.

The dosage of the intravitreal insert may be at least 0.15 μg/day for at least 24 months, at least 0.20 μg/day for at least 24 months, or at least 0.25 μg/day for at least 24 months. Further, the dosage of the intravitreal insert may be from about 0.1 μg/day to about 0.25 μg/day for at least 24 months, from about 0.2 μg/day to about 0.45 μg/day for at least 24 months, or from about 0.3 μg/day to about 0.45 μg/day for at least 24 months.

In another embodiment, the corticosteroid is Fluocinolone Acetonide (FA). The time period of release may be at least eighteen months, at least twenty four months, at least thirty months, or at least thirty six months. In an additional embodiment, the intravitreal insert settles in the posterior portion of the eye after being inserted.

The intravitreal insert may comprise a polyimide tube, Fluocinolone Acetonide, and a polyvinyl alcohol matrix. The insert may comprise from 100 to 300 μg of Fluocinolone Acetonide, from 180 to 200 µg of Fluocinolone Acetonide, and/or 190 µg of Fluocinolone Acetonide. The insert may be non-bioerodable.

In accordance with a second aspect of the invention, a method of administering a corticosteroid to the eye wherein the incidence of IOP lowering surgery at 1 year or more after treatment is less than 10% comprises injecting at least one free-floating intravitreal insert comprising a corticosteroid into an eye of a subject such that the intravitreal insert settles near the base of the eye. The at least one intravitreal insert is configured to release the corticosteroid in a controlled manner over a time period of at least one year.

In accordance with a third aspect of the invention, a method of reducing the incidence of IOP lowering surgeries in patients receiving intraocular treatment with corticosteroids to less than 10% at 1 year or more after treatment comprises injecting at least one free-floating intravitreal insert comprising a corticosteroid into an eye of the subject such that the intravitreal insert settles near the base of the eye. The at least one intravitreal insert is configured to release the corticosteroid in a controlled manner over a time period of at least one year.

DETAILED DESCRIPTION

Figure 1:
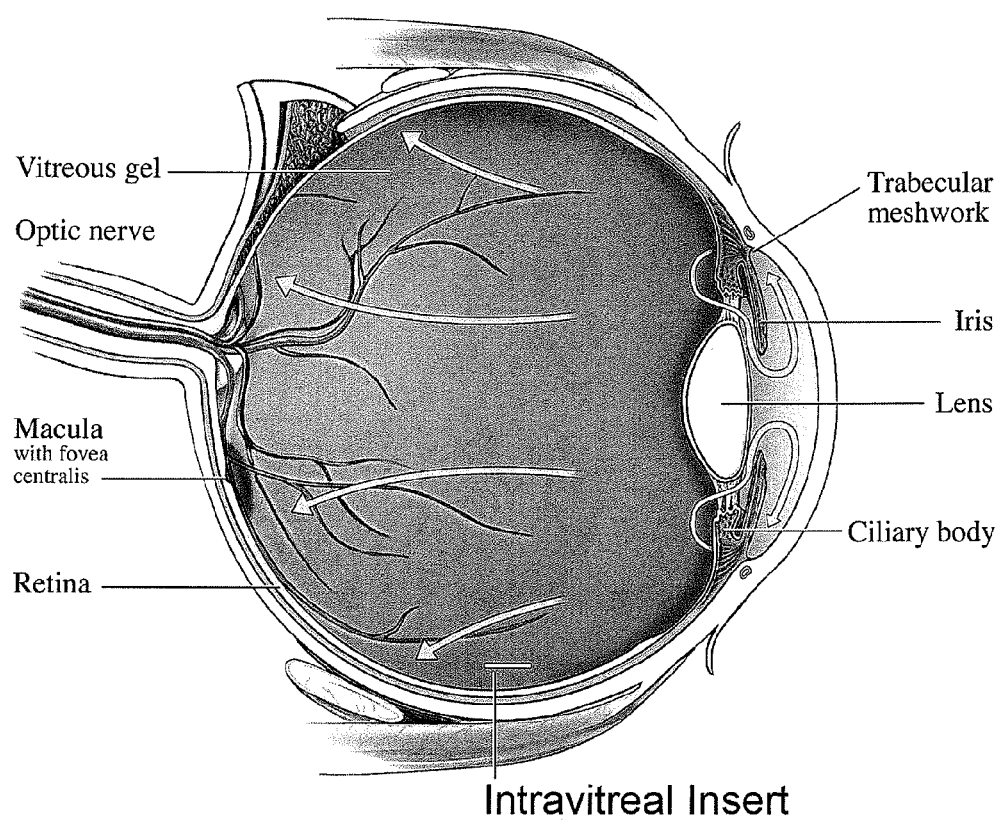
FIG. 1 is a schematic cross-sectional representation of the eye.

The invention relates to a method of treating an ocular disease in a subject using a corticosteroid with reduced incidence of intraocular pressure lowering surgery by injecting an intravitreal insert capable of providing a therapeutic effect for an extended period of time in the treatment of DME. The intravitreal insert delivers sustained sub-microgram levels of corticosteroid in the treatment of ocular disease. Exemplary corticosteroids include, but are not limited to, fluocinolone acetonide (FA), dexamethasone, and triamcinolone acetonide.

The term intravitreal refers to the space inside the eye behind the lens that contains the jelly-like substance called vitreous. In exemplary embodiments, the intravitreal insert is inserted into the back of a patient's eye using an insertion device employing a 25-gauge needle, which allows for a self-sealing wound. This insertion is similar to the administration of an intravitreal injection, a procedure commonly employed by retinal specialists. The insertion procedure is typically non-surgical and is performed in the retinal specialist's office. In an exemplary embodiment, the insert may include a 3.5 mm polyimide tube sealed with an impermeable member at one end, a permeable coating of polyvinyl alcohol at the other end, and a drug core residing within the polyimide tube, such as Illuvien™. The drug core may include a mixture of polyvinyl alcohol and fluocinolone acetonide. The drug core may be cured and the thickness of the permeable coating of polyvinyl alcohol may be adjusted to achieve the desired rate of release.

It is believed that the intravitreal insert improves vision while reducing side effects commonly associated with the use of corticosteroids in the eye. In exemplary embodiments, the active pharmaceutical ingredient in the intravitreal insert is FA, which has demonstrated efficacy in the treatment of DME. The intravitreal insert delivers sustained sub-microgram levels of a corticosteroid to the eye. The intravitreal insert may have a relatively high dosage or a relatively low dosage. For example, a high-dose example may include an insert having an initial release rate of approximately 0.45 µg per day, and a low-dose example may include an insert having an initial release rate of approximately 0.23 µg per day. The dosage levels of currently available corticosteroids for intraocular administration are higher than the exemplary levels of the intravitreal insert described herein. It is believed that the higher dosage levels of currently available corticosteroids for intraocular administration may contribute to adverse side effects related to increased IOP.

The intravitreal insert can be configured to deliver a therapeutic effect for variable durations. For example, the dosage duration may be at least 12 months, at least 18 months, at least 24 months, at least 30 months and/or at least 36 months. It is believed that the intravitreal insert can provide sustained therapy for up to 36 months.

The intravitreal insert can provide sustained delivery of sub-microgram levels of FA over time. For example, in embodiments, the high-dose intravitreal insert may deliver at least 0.1 µg per day, at least 0.15 µg per day, at least 0.2 µg per day, at least 0.25 µg per day, at least 0.3 µg per day, at least 0.35 µg per day, at least 0.4 µg per day, or at least 0.45 µg per day for a dosage duration of at least 12 months, at least 24 months, and/or at least 36 months. In other exemplary embodiments, the low-dose intravitreal insert may deliver at least 0.1 µg per day, at least 0.15 µg per day, at least 0.2 µg per day, or at least 0.23 µg per day for a dosage duration of at least 12 months, at least 24 months, and/or at least 36 months.

The intravitreal insert may be inserted into the eye using a conventional ocular insertion device. For example, the intravitreal insert may be inserted using a device with a 25-gauge needle. Typically, the insertion procedure is non-surgical and may be performed in a retinal specialist's office.

For insertion, the needle of the device is inserted into the eye through the pars plana. The needle is inserted to about the equator of the eye and then the plunger of the device is depressed such that the intravitreal insert is inserted into the vitreous of the eye. After injection, the insert settles at the posterior portion of the eye (distal the pars plana) at or near the vitreous base of the eye. It is believed that this location of the intravitreal insert in the posterior portion of the eye mitigates the incidence of steroid-induced IOP elevations commonly associated with the intraocular use of corticosteroids. FIG. 1 is a schematic cross-sectional representation of the eye. FIG. 1 provides an illustration of the location of the insert in the eye.

As illustrated in FIG. 1, fluid, or aqueous humor, generated at the ciliary body, which is located just behind the iris, flows within the eye primarily via two natural currents of fluid within the eye. The predominant current flows through the iris into the anterior chamber and exits the eye mainly through the trabecular outflow pathway. Another current of outflow, the posterior flow, is directed toward the back of the eye.

Without being bound by theory, it is believed that the side effect of increased IOP associated with corticosteroids in certain people is related to the interaction of corticosteroids with the cells of the trabecular meshwork, a specialized tissue that acts as a filter located in the front of the eye. In some individuals, corticosteroids result in a build-up of debris in this meshwork, increasing resistance to outflow, and increasing pressure inside the eye. It is believed that the positioning of the intravitreal insert in the posterior portion of the eye allows it to take advantage of the posterior flow of fluid away from the trabecular meshwork of the eye. Thus, it is believed that the positioning of the insert combined with its kinetics of release minimize the anterior chamber exposure to FA and mitigates the incidence of IOP elevations and cataract formation commonly associated with the intraocular use of corticosteroids.

The active compound in the intravitreal insert is a corticosteroid. FA will be discussed as an exemplary active compound in the intravitreal insert. However, one of ordinary skill in the art will understand that other corticosteroids may be used. Corticosteroids have demonstrated a range of pharmacological actions, including inhibition of inflammation, inhibition of leukostasis, upregulation of occluding, inhibition of release of certain inflammatory cytokines and suppression of VEGF secretion. These pharmacological actions have the potential to treat various ocular conditions, including DME, dry Age-Related Macular Degeneration (AMD), wet AMD and Retinal Vein Occlusion (RVO). However, FA may exhibit many of the same side effects as other corticosteroids currently available for intraocular use, including increased IOP, which may increase the risk of glaucoma and cataract formation. Corticosteroids are known to cause various IOP related adverse events in patients. For example, as a result of increased IOP, often IOP-lowering surgeries are performed after treatment with corticosteroids. For the product commercially available as RETISERT® (which is a 0.59 mg implant of fluocinolone acetonide), within an average post-implantation period of approximately 2 years, approximately 32% of patients are expected to require filtering procedures to control intraocular pressure. Within an average post-implantation period of approximately 3 years, approximately 37% of patients are expected to require filtering procedures to control intraocular pressure. A three year clinical study of RETISERT® at dosage forms of 0.59 mg and 2.1 mg was performed to determine the effect of RETISERT® on IOP. For the 0.59 mg dosage form, the percentage of patients requiring IOP-lowering surgery at 1 year, 2 years, and 3 years after implantation was 10.9%, 25.9%, and 32%, respectively. For the 2.1 mg dosage form, the percentage of patients requiring IOP-lowering surgery at 1 year, 2 years, and 3 years after implantation was 14.1%, 31.4%, and 41.4%, respectively. Thus, any reduction in the incidence of IOP-lowering surgeries is advantageous.

Without being bound by any theory, it is believed that higher concentration dosages of corticosteroids in the eye may contribute to adverse side effects, such as increased IOP. Advantageously, the present insert is effective even when used in lower concentration dosages (e.g., 0.23 µg/day). Thus, it is believed that the intravitreal insert's ability to deliver sub-microgram levels of FA mitigates the incidence of IOP elevations and cataract formation commonly associated with the intraocular use of corticosteroids.

Additionally, as will be discussed further in the Examples, the incidence of IOP lowering surgeries after treatment with the intravitreal insert is reduced in comparison to current corticosteroid treatment options. For example, the incidence of IOP lowering surgery at 1 year after treatment may be less than 10%, or less than 5%. That is, at 1 year after treatment (i.e., insertion) with the intravitreal insert, less than 10%, or less than 5% of subjects receiving the intravitreal insert will need IOP lowering surgery. In another example, the incidence of IOP lowering surgery at 2 years after treatment may be less than 20%, less than 15%, less than 10%, or less than 5%. In a further example, the incidence of IOP lowering surgery at 3 years after treatment may be less than 30%, less than 25%, less than 20%, less than 15%, less than 10%, or less than 5%.

In an exemplary embodiment, the intravitreal insert comprises a tiny polyimide tube with two permeable polyvinyl alcohol membrane caps or one permeable membrane cap and one impermeable cap that is filled with FA in a polyvinyl alcohol matrix. The insert may comprise varying amounts of FA. For example, the insert may comprise from 100 to 300 µg of FA, from 150 to 250 µg of FA, from 180 to 220 µg, from 180 to 200 µg, or 190 µg of FA. The insert is non-bioerodable; however, both polyimide and the polyvinyl alcohol matrix are biocompatible with ocular tissues and have histories of safe use within the eye. The intravitreal insert can provide sustained sub-microgram levels of FA and a therapeutic effect for up to 36 months.

Figure 2:
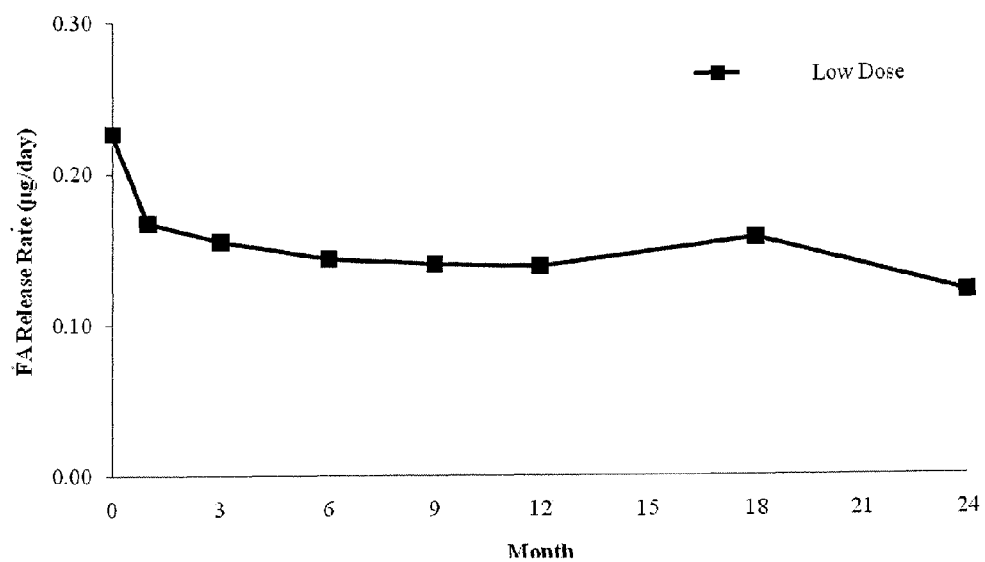
FIG. 2 is a chart showing the FA release rate in µg/day over time for a low dose embodiment of the intravitreal insert.

FIG. 2 is a chart showing the FA release rate in µg/day over time for the low dose embodiment of the intravitreal insert. FIG. 2 includes in vitro data from multiple clinical supply batches of the low dose of the intravitreal insert. It shows that the daily amount of FA released starts at an average daily release rate 0.23 µg per day and continues to release at the month 24 time point. While data points beyond 24 months are not shown, given the available trend, it is contemplated that the FA continues to be released from the intravitreal insert beyond 24 months.

While the intravitreal insert has been discussed for use in treating DME. It is believed that the intravitreal insert may have the potential to address other ophthalmic diseases. Exemplary diseases include, but are not limited to, dry Age-related macular degeneration (AMD), wet AMD and RVO.

EXAMPLES

Clinical trials to assess the efficacy and safety of the intravitreal insert in the treatment of DME have been performed. The trials involved 956 patients in sites across the United States, Canada, Europe and India. A number of assessments were performed using the trial data including assessments related to the patients' best corrected visual acuity (BCVA), measurements and comparisons of excess fovial thickness, and safety or adverse event assessments.

In the trials, the difference in the percentage of patients whose BCVA improved from baseline by 15 or more letters on the Early Treatment Diabetic Retinopathy Study (ETDRS) eye chart between the treatment and control groups at month 24 was measured. The ETDRS eye chart is the standard used in clinical trials for measuring sharpness of sight as established by the National Eye Institute's Early Treatment Diabetic Retinopathy Study. In addition, a numerical comparison of the percentage of patients with BCVA improvement of 15 or more letters between the month 24 and month 18 data was performed to determine if the month 24 results were equal to or greater than the month 18 results.

Example 1

A study was performed to assess the safety and efficacy of the intravitreal insert in patients with DME involving the center of the macula. All patients had previously had at least one prior macular laser treatment 12 weeks or more before study entry. The inclusion criteria for the study were designed to select DME patients with BCVA between 20/50 (68 letters on the ETDRS eye chart) and 20/400 (19 letters on the ETDRS eye chart) in the study eye and no worse than 20/400 in the non-study eye. Patients who had received steroid drug treatments for DME within three months of screening or anti-VEGF injections within two months of screening, and patients with glaucoma, ocular hypertension, IOP greater than 21 mmHg or concurrent therapy with IOP-lowering agents in the study eye at screening were not eligible to participate in this trial.

The study included Trial A and Trial B patients. Trial A and Trial B had identical protocols and included a total of 956 patients across 101 academic and private practice centers. Trial A drew patients from sites located in the northern regions of the United States, Europe and India and all sites in Canada, while sites in the southern regions of the United States, India and Europe comprised Trial B.

Table 1 describes the baseline characteristics of the patients randomized into the study.

TABLE 1

|  | Trial A | | | Trial B | | |
| --- | --- | --- | --- | --- | --- | --- |
|  | Control | Low Dose | High Dose | Control | Low Dose | High Dose |
| Number of Patients | 95 | 190 | 196 | 90 | 186 | 199 |
| Mean Age (years) | 62.7 | 64.0 | 62.3 | 61.1 | 61.8 | 62.2 |
| Mean Baseline Vision (letters) | 54.8 | 53.4 | 52.5 | 54.7 | 53.3 | 53.3 |
| Male/Female (percent) | 50.5/49.5 | 57.9/42.1 | 60.2/39.8 | 66.7/33.3 | 56.5/43.5 | 63.8/36.2 |
| Mean Time Since Diagnosis (years) |  |  |  |  |  |  |
| Diabetes | 16.5 | 17.4 | 16.5 | 16.3 | 16.8 | 15.9 |
| DME | 4.4 | 3.9 | 3.9 | 3.5 | 3.3 | 3.3 |

Patient characteristics, such as age, gender and baseline BCVA, were balanced across the treatment and control groups. As part of randomization, the patients were divided into two separate groups, those with a baseline BCVA score greater than or equal to 49 letters on the ETDRS eye chart and those with a baseline BCVA score of less than 49 letters on the ETDRS eye chart.

Patients were randomly assigned to one of three groups at a ratio of 2:2:1. The first two of these groups were assigned to an active drug formulation and the third group served as the control group, undergoing a sham insertion procedure designed to mimic an intravitreal insertion. The treatment groups consisted of one group receiving a low dose of the intravitreal insert and another group receiving a high dose of the intravitreal insert. To reduce potential bias, the trials used a randomized, double-masked study design so that neither the patient nor the investigational staff involved with assessing the patient knew to which group the patient belonged. In order to simulate an insertion and help to maintain proper patient masking, the sham insertion procedure included all steps involved in the insertion procedure, except that a blunt inserter without a needle was used to apply pressure to the anesthetized eye.

As part of the study, investigators were able to re-treat each patient with the intravitreal insert following their month 12 follow up visit. Through month 24, 24.5% of patients had been treated with more than one intravitreal insert and 2.5% of patients had been treated with three or more intravitreal inserts.

An efficacy endpoint for the study was the difference in the percentage of patients with improved BCVA from baseline of 15 or more letters on the ETDRS eye chart at month 24 between the treatment and control groups.

The full data set includes all 956 patients randomized into the study, with data imputation employed, using "last observation carried forward" (LOCF), for data missing because of patients who discontinued the trial or were unavailable for follow-up (the Full Analysis Set). As part of the analyses, statistical significance based on the Hochberg-Bonferroni procedure (H-B procedure), a procedure employed to control for multiple comparisons, was determined. A target p-value adjustment of 0.0001 was made to account for each of the nine instances when an independent data safety monitoring board reviewed unmasked interim clinical data. These adjustments resulted in a required p-value of 0.0491 or lower for each of Trial A and Trial B to demonstrate statistical significance for both the low dose and high dose of the intravitreal insert. Based upon the H-B procedure, if either dose of the intravitreal insert in a trial did not meet statistical significance, the alternate dose was required to achieve a p-value of 0.02455 or lower in that trial to demonstrate statistical significance.

In the Full Analysis Set, the efficacy endpoint was met with statistical significance for both the low dose and the high dose of the intravitreal insert in Trial A and Trial B, as well as on a combined basis. Table 2 below summarizes the BCVA comparison results.

TABLE 2

Patients Gaining At Least 15 Letters At Month 24

| | Trial A | | | Trial B | | | Combined | | |
| --- | --- | --- | --- | --- | --- | --- | --- | --- | --- |
| Study Group | Individuals | % | p-value | Individuals | % | p-value | Individuals | % | p-value |
| Control | 14/95 | 14.7% | — | 16/90 | 17.8% | — | 30/185 | 16.2% | — |
| Low Dose | 51/190 | 26.8% | 0.029 | 57/186 | 30.6% | 0.030 | 108/376 | 28.7% | 0.002 |
| High Dose | 51/196 | 26.0% | 0.034 | 62/199 | 31.2% | 0.027 | 113/395 | 28.6% | 0.002 |

Additionally, a numerical comparison of the responder rates at month 18 and month 24 in the Full Analysis Set demonstrated that the responder rates for both the low dose and high dose of the intravitreal insert at month 24 were numerically greater than the month 18 responder rates in both Trial A and Trial B.

Example 2

The study protocol provided for analyses of additional data sets. The all-randomized and treated additional data set included 953 patients randomized into the study and treated, with data imputation employed, using the LOCF method, for data missing because of patients who discontinued the trial or are unavailable for follow-up (the ART Data Set). Three patients who were randomized, but not treated, are included in the Full Data Set and excluded from the ART Data Set. In the ART Data Set, the efficacy endpoint was met with statistical significance for both doses of the intravitreal insert in both Trial A and Trial B. The percentage of patients in the ART Data Set achieving improved BCVA of 15 or more letters at month 24 for Trial A was 14.7% for the control group, 26.8% for the low dose (p-value 0.029) and 26.2% for the high dose (p-value 0.032). The percentage of patients in the ART Data Set achieving improved BCVA of 15 or more letters at month 24 for Trial B was 17.8% for the control group, 30.8% for the low dose (p-value 0.028) and 31.3% for the high dose (p-value 0.026).

Example 3

A modified ART Data Set included all 953 patients included in the ART Data Set and excluded data collected subsequent to the use of treatments prohibited by the protocol, such as Avastin, Lucentis, triamcinolone acetonide or vitrectomy (the Modified ART Data Set). In instances when a treatment prohibited by the study protocol was used, the last observation prior to the protocol violation was imputed forward to month 24 using the LOCF method. The percentage of patients in the Modified ART Data Set achieving improved BCVA of 15 or more letters for Trial A was 12.6% for the control group, 22.6% for the low dose (p-value 0.057) and 24.1% for the high dose (p-value 0.026). Neither dose of the intravitreal insert for Trial A was statistically significant based on the H-B procedure. The percentage of patients in the Modified ART Data Set achieving improved BCVA of 15 or more letters at month 24 for Trial B was 13.3% for the control group, 29.7% for the low dose (p-value 0.004) and 29.3% for the high dose (p-value 0.005). Both doses of the intravitreal insert for Trial B were statistically significant.

Example 4

A number of clinically relevant results in the month 24 clinical data from the study were observed. These observations included, among others, the following:

- patients with improved BCVA of 15 or more letters at each follow up visit;
- patients with improved BCVA of 15 or more letters at any time point;
- other levels of BCVA improvement at month 24;
- BCVA improvement of 15 or more letters relative to baseline BCVA; and
- decrease in excess foveal thickness.

The analyses of the Full Analysis Set observations, set forth below, are presented for Trial A and Trial B on a combined basis for patients who received the low dose of the intravitreal insert in comparison to the control group.

Figure 3:
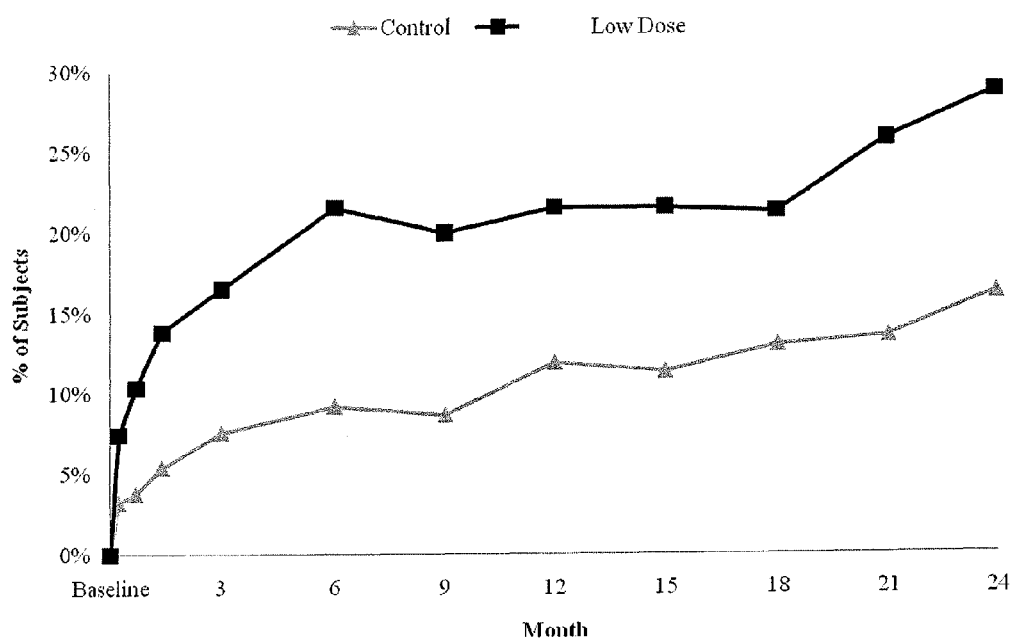
FIG. 3 is a chart showing the responder rate percent over time for BCVA analysis.

Analysis of the results of the study through month 24 indicated that the low dose of the intravitreal insert provides an improvement in BCVA as early as three weeks after insertion. The low dose of the intravitreal insert was statistically significantly better than the control group in the study by week 3 of patient follow up, and maintained a statistically significant advantage over the control through month 24. FIG. 3 is a chart showing the responder rate percent over time for the control group and the low dose group. The responder rate is measured as the improvement in BCVA of 15 letters or more, at each scheduled follow up visit during the study.

As can be seen in FIG. 3, a significantly greater percentage of patients receiving the low dose of the intravitreal insert versus the control group had an improvement in BCVA of 15 letters or more when assessed at any follow up visit. During the 24 months of the study, 177 out of 376 patients randomized to receive the low dose of the intravitreal insert, or 47.1%, demonstrated improved BCVA of 15 letters or more at any time point compared to 51 out of 185 patients, or 27.6%, randomized to the control group.

Table 3 below demonstrates the low dose of the intravitreal insert's statistically significant improvements in BCVA versus the control group at month 24 of the study.

TABLE 3

| Trial A & Trial B Combined | | | |
|---|---|---|---|
| BCVA Improvement | Control | Low Dose | p-value |
| ≧1 letter | 54.1% | 66.8% | 0.005 |
| ≧5 letters | 40.0% | 52.1% | 0.010 |
| ≧10 letters | 26.5% | 38.3% | 0.009 |

The results of the study at month 24 indicated that the intravitreal insert has a statistically significant advantage over the control group irrespective of the severity of a patient's baseline BCVA. Table 4 demonstrates the statistically significant treatment effect of the intravitreal insert versus the control group in patients with baseline BCVA of more than 49 letters on the EDTRS eye chart, and patients with BCVA of 49 letters or less on the EDTRS eye chart at baseline.

TABLE 4

| Trial A & Trial B Combined | | | |
|---|---|---|---|
| Baseline BCVA | Control | Low Dose | p-value |
| Greater Than 49 letters | 11.8% | 21.1% | 0.027 |
| 49 Letters or Less | 28.6% | 46.1% | 0.039 |

Example 5

Figure 4:
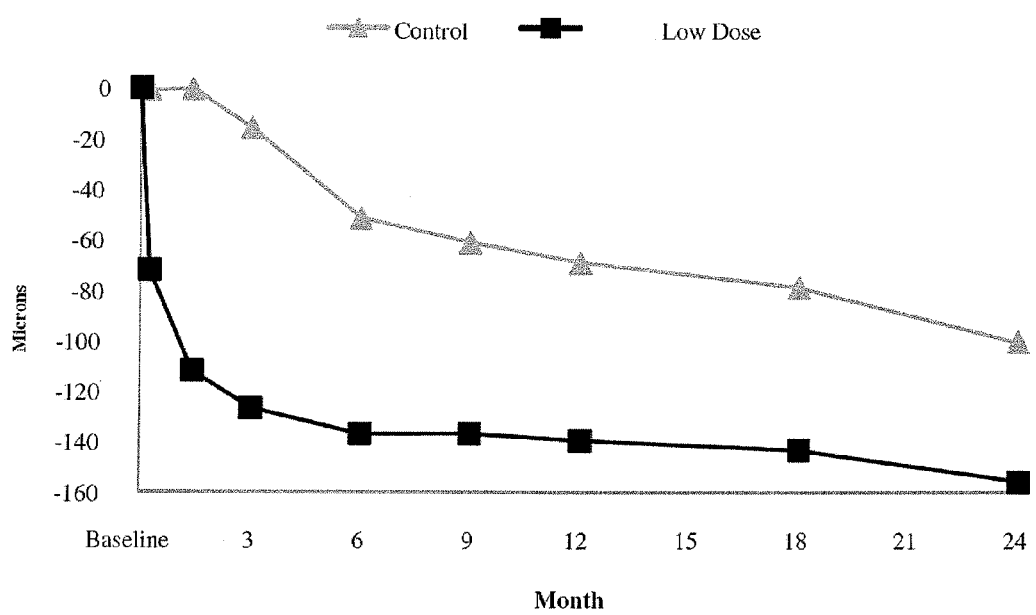
FIG. 4 is a chart summarizing clinical results with regard to excess fovial thickness.

In addition to the functional measures of BCVA, the effect of the intravitreal insert was assessed using an anatomic measure, namely the decrease in excess foveal thickness as determined by optical coherence tomography. Excess foveal thickness is a measurement of the swelling of the macula at its center point (known as the fovea). For the purposes of this application, any measurement above 180 microns was considered to represent excess foveal thickness. FIG. 4 provides a chart summarizing the clinical results of the trial. As shown in FIG. 4, patients receiving the low dose of the intravitreal insert demonstrated a statistically significant difference versus the control group in decreasing excess foveal thickness by week 1 of patient follow up of the study, and maintained a statistically significant advantage through month 24. At month 24, patients receiving the low dose of the intravitreal insert demonstrated a mean decrease in excess foveal thickness of 156.1 microns versus 100.5 microns for the control group.

Example 6

The intravitreal insert was well tolerated through month 24 of the study in both the low and high dose patient populations.

Some reported adverse events occurred beyond patients' 24 month follow up visit; however, all adverse events were included in the data in Table 5 below. The preliminary assessment of adverse event data indicates that there is no apparent risk of systemic adverse events to patients as a result of the use of the intravitreal insert. The use of corticosteroids in the eye is primarily associated with two undesirable side effects: increased IOP, which may increase the risk of glaucoma and require additional procedures to manage, and cataract formation. Excluding IOP related side effects and cataracts, no significant eye related adverse events were observed when comparing both the low dose and high dose patient populations to control. An IOP of 30 mmHg was the clinically significant level that was used in assessing adverse events.

Table 5 below summarizes the IOP related adverse events occurring in all patients randomized and treated in the study.

TABLE 5

| Trial A & Trial B Combined | | | |
|---|---|---|---|
| | Control N = 185 | Low Dose N = 375 | High Dose N = 393 |
| IOP > 30 mmHg[(1)] | 2.7% | 16.3% | 21.6% |
| Trabeculoplasty | 0.0% | 1.3% | 2.5% |
| IOP-Lowering Surgeries | | | |
| Trabeculectomy (filtration) | 0.0% | 2.1% | 5.1% |
| Vitrectomy | 0.0% | 0.3% | 0.5% |
| Other Surgery Performed | 0.5% | 1.3% | 2.5% |
| Percentage of Patients Requiring One or More IOP-Lowering Surgeries | 0.5% | 3.5% | 7.4% |

[(1)]An IOP of 30 mmHg is a clinically significant level that we use in assessing adverse events.

As discussed previously, RETISERT® is a sustained release, intravitreal implant with FA as the active corticosteroid. Studies performed using RETISERT® have shown that the incidence of IOP lowering-surgeries required after implantation thereof are as follows. For the 0.59 mg dosage form, the percentage of patients requiring IOP-lowering surgery at 1 year, 2 years, and 3 years after implantation was 10.9%, 25.9%, and 32%, respectively. For the 2.1 mg dosage form, the percentage of patients requiring IOP-lowering surgery at 1 year, 2 years, and 3 years after implantation was 14.1%, 31.4%, and 41.4%, respectively.

Table 6 below provides a comparison of the incidence of IOP-lowering surgeries performed after treatment with RETISERT® with that for the intravitreal insert. As shown in Table 6, the incidence of IOP-lowering surgeries performed after treatment with the intravitreal insert is surprisingly and unexpectedly low in comparison to those performed after treatment with RETISERT®. In fact, the actual incidence of surgeries after treatment with the intravitreal insert was 66% lower than expected for the low dose intravitreal insert and 63% lower than expected for the high dose intravitreal insert based on the incidence of IOP-lowering surgeries after treatment with RETISERT®.

TABLE 6

| Dosage Form | Level of Steroid Released | Actual Incidence of IOP lowering surgery at 2 years after treatment | Expected Incidence of IOP lowering surgery for Insert based on Retisert data | Difference between Actual and Expected Incidence of IOP lowering surgery |
|---|---|---|---|---|
| Retisert | 0.59 µg/d | 25.9% | | |
| High Dose Insert | 0.45 µg/d | 7.4% | 19.8%[1] | 63% lower |
| Low Dose Insert | 0.23 µg/d | 3.7% | 10.9% | 66% lower |

[1]Calculations as follows:
For HD:
(0.45 µg/d)/(0.59 µg/d) = 0.76 = factor multiplier between dosage of high dose and dosage of Retisert ®
0.76 * 25.9% = 19.8 = expected incidence of surgery for high dose based on incidence for Retisert ®
For LD:
(0.23 µg/d)/(0.59 µg/d) = 0.39 = factor multiplier between dosage of low dose and dosage of Retisert ®
0.39 * 25.9% = 10.9% = expected incidence of surgery for low dose based on incidence for Retisert ®

I claim:

1. A method of treating an ocular disease in a subject using Fluocinolone Acetonide, wherein the incidence of intraocular pressure lowering surgery at 1 year or more after treatment is less than 10%, comprising injecting at least one free-floating non-bioerodable intravitreal insert comprising a dosage of Fluocinolone Acetonide into an eye of the subject such that the intravitreal insert settles near the base of the eye, wherein the intravitreal insert is configured to release Fluocinolone Acetonide in a controlled manner over a time period of at least one year,
    wherein the dosage of the at least one intravitreal insert is from about 0.1 µg/day to about 0.45 µg/day for at least 24 months.

2. The method of claim 1, wherein the ocular disease is diabetic macular edema.

3. The method of claim 1, wherein the incidence of intraocular pressure lowering surgery at 1 year after treatment is less than 5%.

4. The method of claim 1, wherein the incidence of intraocular pressure lowering surgery at 2 years after treatment is less than 10%.

5. The method of claim 4, wherein the incidence of intraocular pressure lowering surgery at 2 years after treatment is less than 5%.

6. The method of claim 1, wherein the incidence of intraocular pressure lowering surgery at 3 years after treatment is less than 10%.

7. The method of claim 1, wherein the dosage of the at least one intravitreal insert is from about 0.15 µg/day to about 0.45 µg/day for at least 24 months.

8. The method of claim 7, wherein the dosage of the at least one intravitreal insert is from about 0.20 µg/day to about 0.45 µg/day for at least 24 months.

9. The method of claim 8, wherein the dosage of the at least one intravitreal insert is from about 0.25 µg/day to about 0.45 µg/day for at least 24 months.

10. The method of claim 1, wherein the dosage of the at least one intravitreal insert is from about 0.1 µg/day to about 0.25 µg/day for at least 24 months.

11. The method of claim 1, wherein the dosage of the at least one intravitreal insert is from about 0.3 μg/day to about 0.45 μg/day for at least 24 months.

12. The method of claim 1, wherein the time period of release is at least thirty months.

13. The method of claim 12, wherein the time period of release is at least thirty six months.

14. The method of claim 1, wherein the at least one intravitreal insert settles in the posterior portion of the eye after being inserted.

15. The method of claim 1, wherein the at least one intravitreal insert comprises a polyimide tube, Fluocinolone Acetonide, and a polyvinyl alcohol matrix.

16. The method of claim 1, wherein the at least one insert comprises from 100 to 300 μg of Fluocinolone Acetonide.

17. The method of claim 16, wherein the at least one insert comprises from 180 to 200 μg of Fluocinolone Acetonide.

18. The method of claim 17, wherein the at least one insert comprises 190 μg of Fluocinolone Acetonide.

19. A method of administering Fluocinolone Acetonide to the eye wherein the incidence of intraocular pressure lowering surgery at 1 year or more after treatment is less than 10%, comprising injecting at least one free-floating non-bioerodable intravitreal insert comprising Fluocinolone Acetonide into an eye of a subject such that the intravitreal insert settles near the base of the eye, wherein the intravitreal insert is configured to release Fluocinolone Acetonide in a controlled manner over a time period of at least one year, wherein the dosage of the at least one intravitreal insert is from about 0.1 μg/day to about 0.45 μg/day for at least 24 months.

20. A method of reducing the incidence of intraocular pressure lowering surgeries in patients receiving intraocular treatment with Fluocinolone Acetonide to less than 10% at 1 year or more after treatment, comprising injecting at least one free-floating non-bioerodable intravitreal insert comprising Fluocinolone Acetonide into an eye of the subject such that the intravitreal insert settles near the base of the eye, wherein the intravitreal insert is configured to release Fluocinolone Acetonide in a controlled manner over a time period of at least one year, wherein the dosage of the at least one intravitreal insert is from about 0.1 μg/day to about 0.45 μg/day for at least 24 months.

* * * * *